United States Patent [19]

Rokugawa et al.

[11] Patent Number: 4,714,672

[45] Date of Patent: Dec. 22, 1987

[54] IMMUNOASSAYS INVOLVING COMPLEMENT LYSING OF CHROMOPHORE CONTAINING MICROCAPSULES

[75] Inventors: Kyuji Rokugawa; Yasuko Tamayama, both of Ootawara, Japan

[73] Assignee: Kabushiki Kaisha Toshiba, Japan

[21] Appl. No.: 618,936

[22] Filed: Jun. 8, 1984

[30] Foreign Application Priority Data

Jun. 14, 1983 [JP] Japan ............................. 58-106345

[51] Int. Cl.$^4$ ................... G01N 33/53; G01N 33/555
[52] U.S. Cl. ............................. 435/7; 436/517; 436/520; 436/522; 436/805; 436/821; 436/829
[58] Field of Search ................. 435/7; 436/517, 520, 436/522, 805, 821, 829

[56] References Cited

U.S. PATENT DOCUMENTS

| 3,819,277 | 6/1974  | Berthelot      | 356/435 |
| 3,850,578 | 11/1974 | McConnell      | 424/12  |
| 4,130,634 | 12/1978 | Molinaro et al.| 424/8   |
| 4,235,792 | 11/1980 | Hsia et al.    | 260/403 |
| 4,305,659 | 12/1981 | Bilstad        | 356/435 |
| 4,372,745 | 2/1983  | Mandle et al.  | 436/805 |
| 4,385,126 | 5/1983  | Chen et al.    | 436/518 |
| 4,483,921 | 11/1984 | Cole           | 435/7   |
| 4,517,303 | 5/1985  | Freytag        | 435/4   |

FOREIGN PATENT DOCUMENTS 2069133  8/1981  United Kingdom .

OTHER PUBLICATIONS

Chemical Abstract, vol. 87, No. 3, 18th Jul. 1977, p. 427, No. 20388g, Columbus, Ohio, Smolarsky et al., "A Simple Fluorescent Method to Determine Complement-Mediated Liposome Immune Lysis" & J. Immunol. Methods 1977, 15(3), 255-65.
Bergmeyer, H. U., *Principles of Enzymatic Analysis*, Verlag Chemie, Weinheim, New York, 1978, p. 142.
*Biochim. Biophys. Acta* 1973 298(2), pp. 158-179, Chemical Abstracts 120694(m) vol. 78, 1973, No. 19.
D'Orzio et al., Ion Electrode Measurements of Complement and Antibody Levels Using Marker-Loaded Sheep Red Blood Cell Ghosts, *Anal. Chem*, vol. 49, No. 13, Nov. 1977, pp. 2083-2086.

*Primary Examiner*—Sidney Marantz
*Assistant Examiner*—Robert Benson
*Attorney, Agent, or Firm*—Finnegan, Henderson, Farabow, Garrett & Dunner

[57] ABSTRACT

An immunoassay of the type which utilizes the hemolysis of microcapsules such as red blood cells. Microcapsules which can be lysed by complement activity, which contain an optically determinable substance, on whose surfaces an antibody to be quantified is bound are prepared. The microcapsules, a test sample containing the antigen or the antibody to be quantified, and complement are mixed to react each other. Thereafter, an optical measurement is conducted at different wavelengths for the reaction mixture which is still suspending the intact microcapsules.

6 Claims, 5 Drawing Figures

IMMUNOASSAYS INVOLVING COMPLEMENT LYSING OF CHROMOPHORE CONTAINING MICROCAPSULES

BACKGROUND OF THE INVENTION

I. Field of the Invention

This invention relates to an immunoassay, and more particularly, this invention relates to an immunoassay of the type which utilizes the lysation of microcapsules such as red blood cells by complement activated by an antigen-antibody complex.

II. Description of the Prior Art

As a conventional immunoassay, radioimmunoassay (RIA) is known in which a specific antigen (or antibody) in a test sample is quantified utilizing the immunological reaction between antibody (or antigen) marked with radioisotope and the antigen (or antibody) in the test sample. However, since the radioisotope has to be determined, the equipment used for RIA is complicated and expensive. Further, several hours to several tens of hours are required for the accurate determination in RIA.

Enzyme immunoassay is also widely known as a conventional immunoassay. In this method, an antigen-antibody complex is obtained by the antigen-antibody reaction between antibody (or antigen) marked with an enzyme and antigen (or antibody) in a test sample. Thereafter, a specific antigen (or antibody) in the sample is determined utilizing the enzyme reaction of the marker enzyme. However, this method also requires several hours to several tens of hours for the accurate quantification of the antigen (or antibody).

As a method of quantifying complement in a serum, so called 50% hemolysis method (CH 50) developed by Meyer is known. In this method, sheep red blood cells sensitized with an optimum amount of hemolysin (anti-sheep red blood cell antibody) are reacted with a serum to be tested at 37° C. for 60 minutes. In doing this, the sensitized sheep red blood cells are lysed by the action of complement in the test serum, so that the complement can be quantified by determining the degree of hemolysis. However, the hemolytic reaction can only be halted by cooling the reaction mixture in an ice bath. Further, in this method, the degree of hemolysis is determined by centrifuging the reaction mixture and measuring the absorbance at 541 nm of the supernatant obtained by the centrifugation. Thus, the procedure is time-consuming and further the test results are not always accurate.

SUMMARY OF THE INVENTION

Accordingly, the object of the present invention is to provide an immunoassay by which antigen or antibody can be quantified accurately in a very short time.

In the immunoassay of the present invention, microcapsules which can be lysed by complement activity, which contain an optically determinable substance, on whose surfaces an antibody or an antigen specific to an antigen or an antibody to be quantified is bound are provided. The microcapsules are mixed with a test sample containing the antigen or antibody to be quantified and with complement. By so doing, an antigen-antibody complex is formed between the antibody or antigen bound on the surfaces of the microcapsules and the corresponding antigen or antibody in the test sample. The complement is activated by the antigen-antibody complex, so that at least some of the microcapsules are lysed by the complement activity. As a result, the optically determinable substance contained in the microcapsules is released from the microcapsules to the reaction mixture. Thereafter an optical measurement is conducted at different wavelengths for the reaction mixture which is still suspending the intact or unlysed microcapsules. The amount of the antigen or antibody in the sample can be known from the difference of the values obtained by the optical measurement.

Since centrifugation of the resultant reaction mixture is not necessary for the optical measurement, the procedure of the immunoassay of the present invention is very simple. Further, accurate assay can be accomplished.

DETAILED DESCRIPTION OF THE PREFERRED EMBODIMENTS

Figure 1:
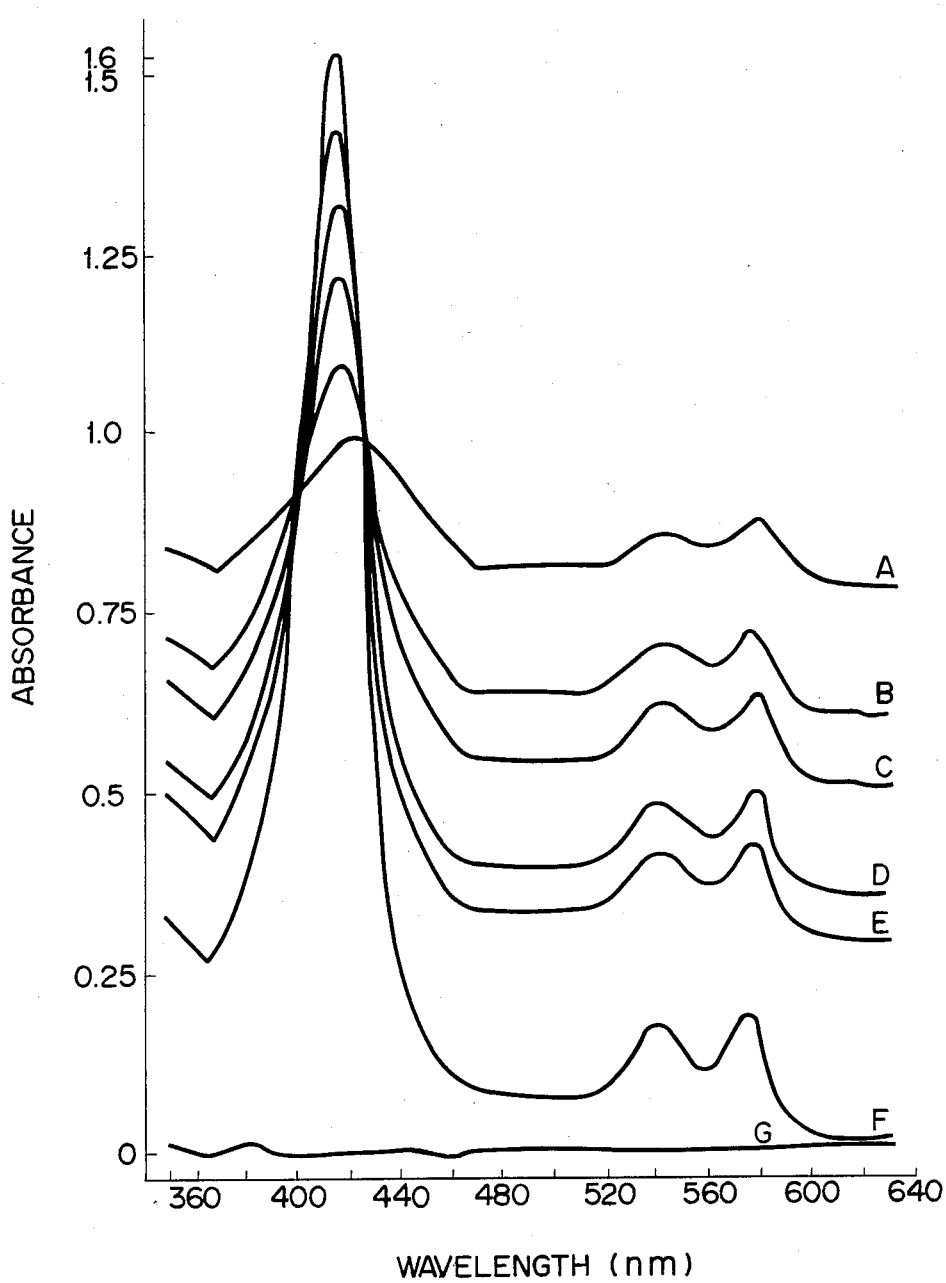
FIG. 1 shows the relationship between the wavelength and the absorbance of red blood cell suspensions with varying hemolysis rate.

In the immunoassay of the present invention, microcapsules which can be lysed by complement activity are used. Preferred examples of the microcapsules include red blood cells (RBC) of animals and artificial microcapsules such as liposomes. Among these, sheep red blood cells are especially preferred since various kinds of antibodies (or antigens) can be bound on the surfaces thereof.

On the outer surfaces of the microcapsules, an antibody (or an antigen) specific to the antigen (or antibody) to be quantified is bound. The antigen (or antibody) to be quantified may be arbitrarily selected. Examples of such antigen (or antibody) to be quantified include α-fetoprotein (α-FP) contained in a blood sample from a patient suffering from cancer, Hepatitis B surface antigen contained in blood from a patient suffering from Hepatitis B, and antiepileptic for treatment of epilepsy. The antibody (or antigen) bound on the surfaces of the microcapsules must be able to specifically complex with the corresponding antigen (or antibody) to be quantified. For example, when α-FP is to be quantified, anti-α-FP antibody must be coupled to the surfaces of the microcapsules.

The microcapsules contain therein an optically determinable substance. The term "optically determinable substance" means the substance which can be quantified by measuring the absorbance, fluorescence or luminescence of a composition containing the substance. Examples of the optically determinable substance include proteins such as hemoglobin and albumin, polynucleotide, fluorescent substances such as fluorescein isothiocyanate and carboxy fluorescein, and luminous substances such as luminol. If RBC are employed as the microcapsules, the hemoglobin inherently included in the RBC can be conveniently used as the optically determinable substance.

The optically determinable substance can be one which can be "indirectly" determined. Thus, an enzyme or a substrate, which produces a readily optically determinable product upon reaction with the corresponding substrate or enzyme, can be used as the optically determinable substance. For example, alkaline phosphatase, which deesterifies p-nitro-phenyl phosphate to produce colored p-nitrophenol, can be contained in the microcapsules. Further, peroxidase, which reacts with hydrogen peroxide in the presence of 4-aminoantipyrine to produce a quinone pigment, can also be used as the optically determinable substance. Instead of encapsulating an enzyme in the microcapsules, a substrate which is catalyzed by an enzyme to produce a colored, fluorescent, or luminous product can also be encapsulated in the microcapsules. Encapsulating a substrate in the microcapsules is preferred to encapsulating an enzyme since an enzyme may possibly be denatured in the microcapsules when the microcapsules are stored for a long time. If the microcapsules contain an enzyme, the enzyme may preferably be contained in excess with respect to the antigen (or antibody) to be quantified. More specifically, the amount of the enzyme may be such that an enzyme activity of the enzyme per 1 ng to 1 $\mu$g of the antigen (or antibody) to be quantified is preferably 100 U/ml or more, and more preferably 500 to 1,000 U/ml. When enzyme is contained in such a large amount, immunoassay can be performed within an extremely short period of time. For example, immunoassay which conventionally takes several tens of hours only takes about 5 to 10 minutes according to the present immunoassay.

The above-described microcapsules may be obtained as follows:

First, the antibody (or antigen) specific to the antigen (or antibody) to be quantified is provided. Such an antibody (or antigen) can be obtained by a conventional well-known method. Further, various kinds of antibodies and antigens are commercially available, and the commercially available antibodies and antigens can conveniently used in the present invention.

Next, the antibody (or antigen) specific to the antigen (or antibody) to be quantified is bound to the surfaces of the microcapsules. Binding the antibody (or antigen) to the surfaces of the microcapsules is also well-known. For example, mixing a red blood cell suspension with the antibody in the presence of tannic acid, chromium chloride or a water-soluble carbodiimide permits the antibody to be bound to the surfaces of the red blood cells.

When the microcapsules employed are RBC, the microcapsules to be used in the present immunoassay can thus be prepared since RBC inherently contain hemoglobin which is an optically determinable substance. However, where another optically determinable substance is preferred to be encapsulated in the RBC, the content in RBC such as hemoglobin can be displaced with the another optically determinable substance by a well-known method. This method is based on the phenomenon that RBC can be re-formed after osmotic lysis under the proper conditions of osmolarity, temperature and pH, to trap any solutes present at the time of re-forming. The detailed procedure is described, for example, by Paul D'Orazlo et al., "Ion Electrode Measurements of Complement and Antibody Levels Using Marker-Loaded Sheep Red Blood Cell Ghosts", Analytical Chemistry, Vol 49, No. 13, which is hereby incorporated by reference. How to encapsulate a substance in liposomes is also well-known in the art and the description thereof will be omitted.

The first step of the immunoassay according to the present invention is to mix the above-described microcapsules, a test sample containing the antigen (or antibody) to be quantified, and complement. The test sample may be, for example, blood, urine, lymph, coelomic fluid, or pancreatic juice. Serum from an animal can be used as it is as the complement, and guinea pig serum is preferred since the complement activity is high. The mixture is then incubated to allow the reaction among the three reagents. Incubation temperature may be, for example, 37° C., and incubation time may be, for example, as short as 5 to 10 minutes.

An antigen-antibody complex is formed between the antibody (or antigen) bound on the surfaces of the microcapsules and the antigen (or antibody) in the test sample. The antigen-antibody complex activates the complement in the mixture, and the microcapusles are then lysed by the complement activity to release the optically determinable substance contained in the microcapsules. The amount of the antigen-antibody complex is proportional to the amount of the antigen (or antibody) contained in the test sample if a constant amount of microcapsules with a constant amount of antibody (or antigen) bound to the surfaces thereof are used. Therefore, in turn, the amount of the released optically determinable substance is proportional to the amount of the antigen (or antibody) in the test sample if the other conditions are set constant. Thus, the antigen (or antibody) in the test sample can be determined by quantifying the released optically determinable substance.

Next step is to quantify the optically determinable substance released from the lysed microcapsules. This can be done, of course, by an optical measurement since the substance is "optically determinable". However, the reaction mixture is usually, or almost always has the intact microcapsules suspended within it, i.e., the microcapsules which were not lysed in the reaction. The intact microcapsules make the optical measurement very difficult since the light impinged on the reaction mixture, or the light from the reaction mixture is scattered by them, so that the specific light signal caused by the released optically determinable substance is significantly weakened. This problem can be solved by centrifuging the reaction mixture to precipitate the intact microcapsules and conducting an optical measurement for the supernatant. However, centrifugation is a troublesome and time-consuming procedure.

According to the immunoassay of the present invention, optical measurement is conducted for the reaction mixture still with suspended intact microcapsules, so that the centrifugation can be omitted. In the present immunoassay, the optical measurement is conducted at different wavelengths. For example, if the optically determinable substance is the hemoglobin inherently contained in RBC, and optical measurement is conducted by determining the absorbance of the reaction mixture, the absorbance at 415 nm (A415) and at 500 nm (A500) may be determined. It has been found by the present inventors that the difference of the absorbance at different wavelengths, for example, A415–A500 has a linear relationship with the ratio of hemolysis, as will be clearly demonstrated in the later described examples. Thus, from the difference of values obtained by optical measurement, the antigen (or antibody) in the test sample can be quantified if a calibration curve is prepared.

Such optical measurment at different wavelengths can be conducted with a usual spectrophotometer which is widely used. Further, the optical measurement at different wavelengths can be conveniently conducted with a spectrophotometer by which absorbance at different wavelengths is simultaneously measured and the difference between them is outputted. Such a spectrophotometer is known in the art and is described, for example, by Hisayuki Sagusa et al., U.S. Pat. No. 4,318,615, issued on Mar. 9, 1982, which is hereby incorporated by reference.

How to prepare a calibration curve is well-known in the field of immunoassay. More specifically, in the present immunoassay, a test sample containing a known concentration of antigen (or antibody) is subjected to the present immunoassay to obtain the difference of the values (such as absorbance) determined in the optical measurement at different wavelengths. Changing the concentration of the antigen (or antibody) in the sample, the procedure is repeated. A calibration curve is prepared by plotting the concentration of the antigen (or antibody) in the sample along the axis of abscissa and the difference of the values measured in the optical measurement along the axis of ordinate. The unknown concentration of the antigen (or antibody) in a test sample can be determined from the calibration curve thus obtained by conducting an immunoassay under the same conditions in which the calibration curve is made.

Figure 3:
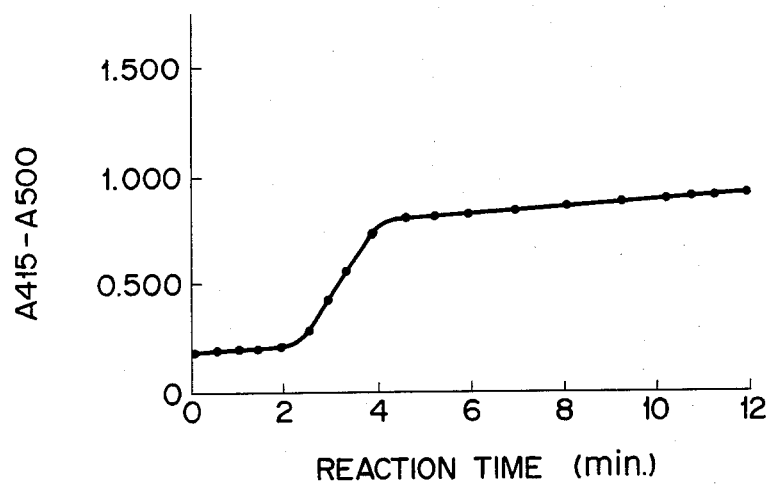
FIG. 3 shows the relationship between the reaction time and the difference between the absorbance at 415 nm and at 500 nm.

Another method of preparing a calibration curve is available in the immunoassay of the present invention. This method is a kind of so called "rate assay". More specifically, a sample containing a known concentration of antigen (or antibody) is subjected to the immunoassay of the present invention, and this time, the difference of the values at different wavelengths is continuously or periodically recorded from the beginning of the reaction. Continuous recording can be accomplished by using a spectrophotometer with a flow chart recorder. Plotting the reaction time along the axis of abscissa and the difference of the values at different wavelengths along the axis of ordinate, a curve as shown in FIG. 3 is obtained (this figure will be later described in detail). As can be seen from FIG. 3, after about 2 minutes from the beginning of the reaction, the difference of the absorbance (i.e., A415-A500) linearly increase to reach a saturated level after about 4 minutes. The slope of the linearly increasing region (i.e., A415-A500/min.) is recorded. The procedure is repeated changing the concentration of the antigen (or antibody) in the sample. A calibration curve can be obtained by plotting the concentration of the antigen (or antibody) in the sample along the axis of abscissa and plotting the rate of change of the difference of the values at different wavelengths (e.g., A415-A500/min.). Unknown concentration of antigen (or antibody) in a sample can be quantified using the calibration curve. If the calibration curve is for such a rate assay, the immunoassay does not have to be conducted under the same conditions in which the calibration curve was prepared. This is because the rate assay is based on the "rate of change" of the difference of the values at different wavelengths, and not based on the "difference" itself.

Above description is directed to the quantification of antigen or antibody in a test sample. However, complement in a test sample can be quantified by a similar method.

EXAMPLE 1

This example is to show that the difference between the absorbance measured at two different wavelengths has the linear relationship with the amount of the released optically determinable substance. Note that this example is not an "example" of the present invention since no reaction was conducted but mechanically destroyed RBC were used.

Figure 2:
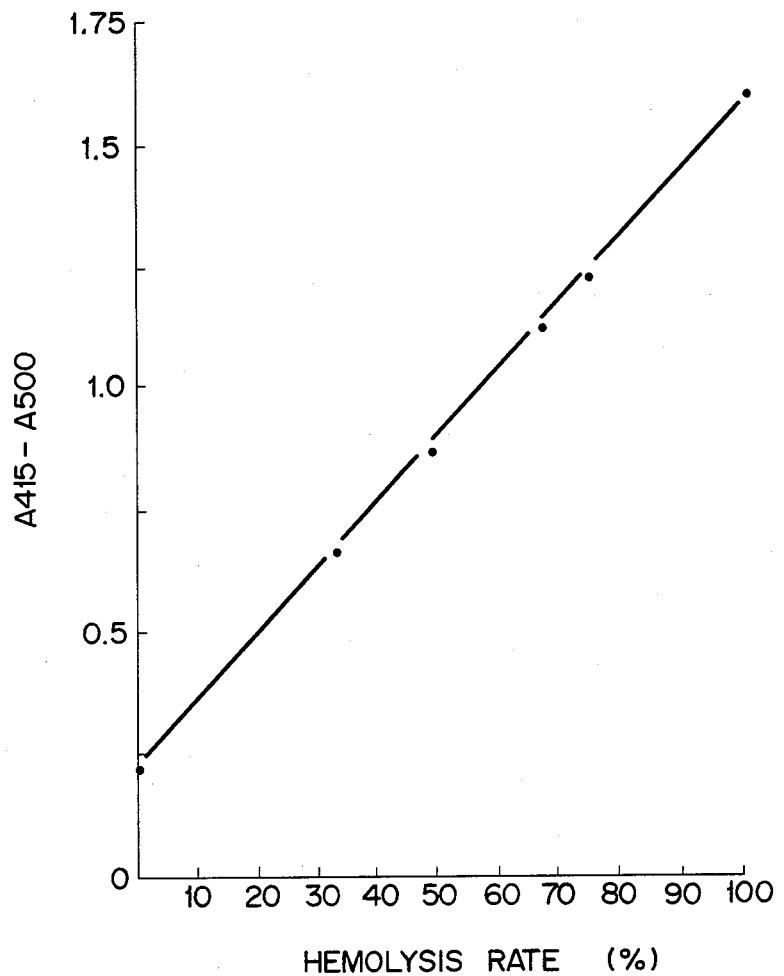
FIG. 2 shows the relationship between the hemolysis rate and the difference between the absorbance at 415 nm and at 500 nm.

First of all, 0.1% by volume of sheep red blood cell (SRBC) suspension in Gelatin-Veronal buffer (GVB) was prepared. Half of the suspension was subjected to a freeze-defreeze cycle to hemolyze the SRBC (this suspension is hereinafter referred to as "hemolyzed fluid"). A series of test tubes each containing an aliquot of the above suspension containing intact SRBC was prepared. To each of the test tubes, a varying amount of the hemolyzed fluid was separately added to obtain a series of mixtures in which the proportion of the hemolyzed SRBC in the total SRBC (hereinafter referred to as hemolysis rate) was 30%, 50%, 60%, and 75%, respectively. The absorbance was measured for the intact SRBC suspension, mixtures having the hemolysis rate of 30%, 50%, 60% and 75%, and the hemolyzed fluid while continuously changing the wavelength of the light impinging on the sample. The results are shown in FIG. 1. In FIG. 1, curves A, B, C, D, E and F respectively show the absorbance-wavelength relations for these mixtures in the order mentioned. Curve G shows the base line of the measurement. From FIG. 1, the difference between the absorbance at 415 nm (A415) which is the peak absorbance of hemoglobin and the absorbance at 500 nm (A500) at which hemoglobin has no absorbance was measured and is plotted with respect to the hemolysis rate, which is shown in FIG. 2. As can be seen from FIG. 2, A415-A500 has a linear relationship with the hemolysis rate. This indicates that the present invention can work.

EXAMPLE 2

Sheep red blood cells coated with anti-SRBC antibodies (commercially available from Denka Seiken Co. Ltd., Tokyo, Japan) were washed with GVB and were suspended in GVB to obtain a sensitized SRBC preparation containing $5 \times 10^8$ cells/ml. Guinea pig serum was diluted 81 times with GVB to obtain a standard complement fluid. The sensitized SRBC preparation and the standard complement fluid was mixed at various ratios shown in the Table below. The mixtures were incubated at 37° C. to lyse the SRBC.

TABLE

| SAMPLE NO. | No. 1 | No. 2 | No. 3 | No. 4 | No. 5 | No. 6 |
|---|---|---|---|---|---|---|
| Standard Complement Fluid | 0 | 0.5 | 1 | 1.5 | 2 | 2.6 |
| GVB | 2.6 | 2.1 | 1.6 | 1.1 | 0.6 | 0 |
| Sensitized SRBC Preparation | 0.4 | 0.4 | 0.4 | 0.4 | 0.4 | 0.4 |

Figure 4:
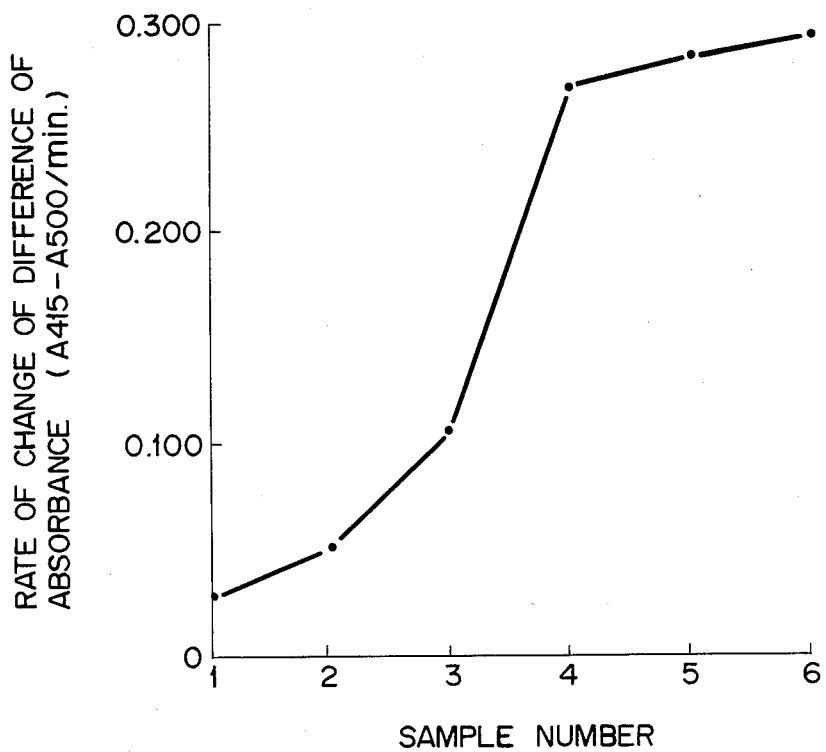
FIG. 4 shows the relationship between the dilution of complement and the rate of change of the difference between the absorbance at 415 nm and at 500 nm.

Next, A415-A500 was periodically determined for the reaction mixtures from the beginning of the reaction. As a representative, the result for the sample No. 6 is shown in FIG. 3. As can be seen from FIG. 3, after about 2 minutes time lag, A415-A500 linearly increased with time and reached a saturated level after about 4 minutes from the beginning of the reaction. The slope of the linearly increasing region, that is, rate of change of A415−A500 (A415−A500/min.) is determined from the graph for every sample. The results are shown in FIG. 4. In FIG. 4, sample No. is taken along the abscissa and the A415−A500/min. is taken along the ordinate. It can be seen from FIG. 4, that A415−A500 varies depending on the concentration of the complement in the sample. This also indicates that the present invention can work.

EXAMPLE 3

Figure 5:
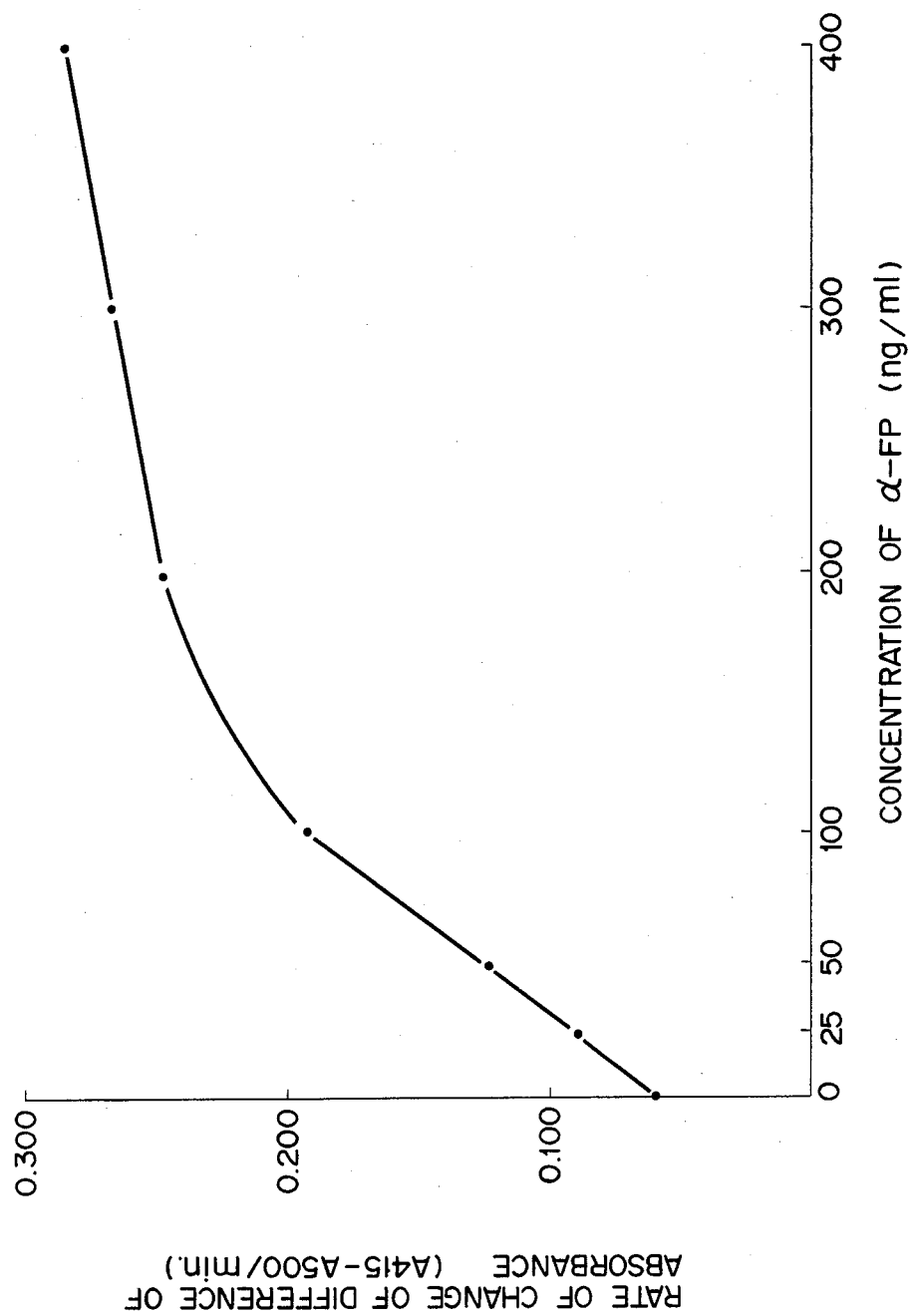
FIG. 5 shows a calibration curve obtained according to the immunoassay of the present invention.

Anti-human α-FP goat antibody was prepared by a conventional manner. Sheep blood was centrifuged and SRBC were collected. The SRBC were washed with physiological saline by centrifugation. One part by volume of a solution of the above antibody in physiological saline (protein content of 1 mg/ml) was added to one part by volume of SRBC precipitation, and 10 parts by volume of an aqueous solution of chromium chloride (67 μg/ml) was added to the mixture. The resultant mixture was left to stand at room temperature for 1 hour. The thus obtained SRBC on whose surfaces anti-human α-FP antibody was bound was washed with physiological saline and then was suspended in physiological saline to attain the concentration of 8% by volume. Then 50 μl of the thus obtained SRBC was placed in a cell for measuring absorbance of which light pass length is 70 mm, and a human serum containing known amount of human α-FP was added to the cell. Thereafter, 1.9 ml of GVB and 1.0 ml of 50-times diluted guinea pig serum were added to the cell and mixed. By the same method described in Example 2, the rate of change of A415−A500 was measured. The relationship between the concentration of α-FP in the human serum and A415−A500/min. is shown in FIG. 5. It can be seen from FIG. 5, that the rate of change of A415−A500 varies depending on the concentration of the α-FP in the sample. Thus, using FIG. 5 as a calibration curve, unknown concentration of α-FP in a test sample can be determined.

What is claimed is:

1. An immunoassay method for quantitatively determining the amount of antigen or antibody in a sample comprising the steps of:

(a) mixing (1) a sample containing antigen or antibody to be quantitatively determined with (2) microcapsules containing an optically determinable substance, said microcapsules having surfaces on which are bound an antibody or an antigen specific to said antigen or antibody to be quantified and (3) a complement which is capable of lysing said microcapsules to form a reaction mixture in which occurs an immune reaction between said antibody or antigen on said surfaces of said microcapsules and said antigen or antibody in said sample, said immune reaction causing said complement to lyse said microcapsules thereby releasing said optically determinable substance from said microcapsules into said reaction mixture;

(b) detecting the absorbance of said reaction mixture during said immune reaction by optical measurements simultaneously at two different wavelengths; and (c) quantifying the amount of said antigen or antibody in said sample by calculating the differences of said absorbances at said different wavelengths.

2. The immunoassay of claim 1, wherein the microcapsules are red blood cells or liposomes.

3. The immunoassay of claim 1, wherein the microcapsules are red blood cells and the optically determinable substance is the hemoglobin inherently contained in the red blood cells.

4. The immunoassay of claim 1, wherein the optically determined substance is an enzyme or a substrate, and after being released from the microcapsules, the enzyme or the substrate is reacted with a corresponding substrate or enzyme to produce a product which can be directly optically determined.

5. The immunoassay of claim 1, wherein the optical measurement is conducted by determining the rate of change of the difference of the absorbances determined at two different wavelengths.

6. The process of claim 1, wherein said different wavelengths comprise one wavelength at which said optically determinable substance is absorbed and another wavelength at which said optically determinable substance is not absorbed.

* * * * *